US00PP19553P2

(12) United States Plant Patent
Nakanishi

(10) Patent No.: US PP19,553 P2
(45) Date of Patent: Dec. 9, 2008

(54) ***PETUNIA* PLANT NAMED 'KUMIYAMA 4'**

(50) Latin Name: *Petunia ×hybrida*
Varietal Denomination: Kumiyama 4

(75) Inventor: Yoshiharu Nakanishi, Kyoto (JP)

(73) Assignee: Suntory Flowers Ltd, Tokyo (JP)

( * ) Notice: Subject to any disclaimer, the term of this patent is extended or adjusted under 35 U.S.C. 154(b) by 0 days.

(21) Appl. No.: 11/787,714

(22) Filed: Apr. 16, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Petunia* plant named 'Kumiyama 4', characterized by its compact, upright, outwardly spreading and mounding plant habit; freely branching and flowering plant habit; and medium-sized light violet-colored flowers with darker violet-colored random sectors and venation.

1 Drawing Sheet

Botanical designation: *Petunia×hybrida.*
Cultivar denomination: 'KUMIYAMA 4'.

BACKGROUND OF THE INVENTION

The present invention relates to a new and distinct cultivar of *Petunia,* botanically known as *Petunia×hybrida* and hereinafter referred to by the name 'Kumiyama 4'.

The new *Petunia* is a product of a planned breeding program conducted by the Inventor in Kyoto, Japan. The objective of the breeding program is to create new *Petunia* cultivars with large and uniquely colored flowers.

The new *Petunia* originated from a cross-pollination made by the Inventor in Kyoto, Japan in April, 2002, of a proprietary selection of *Petunia×hybrida* identified as code number NA-15, not patented, as the female, or seed parent with the *Petunia×hybrida* cultivar Avalanche White, not patented, as the male, or pollen, parent. The cultivar Kumiyama 4 was discovered and selected by the Inventor as a flowering plant from within the progeny of the stated cross-pollination in a controlled environment in Kyoto, Japan.

Asexual reproduction of the new *Petunia* by terminal cuttings in a controlled environment in Kyoto, Japan since April, 2005, has shown that the unique features of this new *Petunia* are stable and reproduced true to type in successive generations.

SUMMARY OF THE INVENTION

The cultivar Kumiyama 4 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kumiyama 4'. These characteristics in combination distinguish 'Kumiyama 4' as a new and distinct cultivar of *Petunia:*

1. Compact, upright, outwardly spreading and mounding plant habit.
2. Freely branching and flowering plant habit.

3. Medium-sized light violet-colored flowers with darker violet-colored random sectors and venation.

Plants of the new *Petunia* can be compared to plants of the female parent selection. Plants of the new *Petunia* differ from plants of the female parent selection in the following characteristics:

1. Plants of the new *Petunia* are more spreading than plants of the female parent selection.
2. Plants of the new *Petunia* have shorter internodes than plants of the female parent selection.
3. Plants of the new *Petunia* have smaller flowers than plants of the female parent selection.
4. Plants of the new *Petunia* and the parent selection differ in flower color as plants of the female parent selection have violet-colored flowers.

Plants of the new *Petunia* can be compared to plants of the male parent, the cultivar Avalanche White. Plants of the new *Petunia* differ from plants of the cultivar Avalanche White in the following characteristics:

1. Plants of the new *Petunia* are more spreading than and not as decumbent as plants of the cultivar Avalanche White.
2. Plants of the new *Petunia* and the parent selection differ in flower color as plants of the cultivar Avalanche White have white-colored flowers.

Plants of the new *Petunia* can also be compared to plants of the cultivar Sunsurfbv, disclosed in U.S. Plant patent application Ser. No. 11/264,781. In side-by-side comparisons conducted in Kyoto, Japan, plants of the new *Petunia* and the cultivar Sunsurfbv differed in the following characteristics:

1. Plants of the new *Petunia* were more spreading than and not as decumbent as plants of the cultivar Sunsurfbv.
2. Plants of the new *Petunia* had larger flowers than plants of the cultivar Sunsurfbv.
3. Plants of the new *Petunia* and the cultivar Sunsurfbv differed in flower color.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a side perspective view of a typical flowering plant of 'Kumiyama 4' grown in a container.

The photograph at the bottom of the sheet comprises a close-up view of a typical flower of 'Kumiyama 4'.

DETAILED BOTANICAL DESCRIPTION

The photographs and following observations, measurements and values describe plants grown in Shiga, Japan, under commercial practice during the autumn in a polyethylene-covered greenhouse. During the production of the plants, day temperatures averaged 23° C. and night temperatures averaged 13° C. Plants were grown for three months with one plant per 13.5-cm container. In the following description, color references are made to The Royal Horticultural Society Colour Chart, 2001 Edition, except where general terms of ordinary dictionary significance are used.

Botanical classification: *Petunia×hybrida* cultivar Kumiyama 4.

Parentage:

*Female, or seed, parent.*—Proprietary selection of *Petunia×hybrida* identified as code number NA-15, not patented.

*Male, or pollen, parent.*—*Petunia×hybrida* cultivar Avalanche White, not patented.

Propagation:

*Type.*—By terminal cuttings.

*Time to initiate roots.*—About one week at 20° C. to 25° C.

*Time to produce a rooted young plant.*—About three weeks at 20° C. to 25° C.

*Root description.*—Fine, fibrous; light brown in color.

*Rooting habit.*—Freely branching.

Plant description:

*Plant and growth habit.*—Compact, upright, outwardly spreading and mounding plant habit. Freely branching; about 13 lateral branches develop per plant. Vigorous growth habit.

*Plant height.*—About 18 cm.

*Plant diameter.*—About 22.5 cm.

Lateral branch description:

*Length.*—About 18 cm.

*Diameter.*—About 1.3 mm.

*Internode length.*—About 1.3 cm.

*Strength.*—Strong.

*Aspect.*—Initially to outwardly spreading.

*Texture.*—Pubescent.

*Color.*—144A.

Foliage description:

*Arrangement.*—Alternate, simple.

*Length.*—About 3 cm.

*Width.*—About 1.8 cm.

*Shape.*—Elliptic to obovate.

*Apex.*—Obtuse.

*Base.*—Attenuate to obtuse.

*Margin.*—Entire.

*Texture, upper and lower surfaces.*—Pubescent; viscid.

*Venation pattern.*—Pinnate; reticulate.

*Color.*—Developing foliage, upper and lower surfaces: 144A. Fully expanded foliage, upper surface: 137C; venation, 144B. Fully expanded foliage, lower surface: 146B; venation, 144B.

*Petiole length.*—About 3.4 mm.

*Petiole diameter.*—About 1.7 mm.

*Petiole texture, upper and lower surfaces.*—Pubescent.

*Petiole color, upper and lower surfaces.*—144B.

Flower description:

*Flower arrangement and habit.*—Single salverform flowers arising from upper leaf axils. Freely flowering habit with usually about 30 flowers developing per plant. Flowers not persistent. Flowers face upright or outwardly. Flowers fragrant.

*Natural flowering season.*—Plants of the new *Petunia* initiate and develop flowers about two to three weeks after planting. Long flowering period; flowering commences naturally during the spring and plants flower continuously throughout the summer until the fall in Japan; flowering continuous.

*Flower longevity.*—Individual flowers last about five days on the plant.

*Flower diameter.*—About 7 cm.

*Flower length (depth).*—About 3.8 cm.

*Tube length.*—About 2.9 cm.

*Flower bud.*—Shape: Cylindrical. Length: About 7.4 cm. Diameter: About 3.7 cm. Color: 150C tinted with N77A.

*Corolla.*—Arrangement: Five petals fused at the base and opening into a flared trumpet. Petal length from throat: About 3.1 cm. Petal width: About 3.5 cm. Petal shape: Broadly obovate. Petal apex: Cuspidate. Petal margin: Entire; slightly undulate. Petal texture, upper and lower surfaces: Smooth, glabrous; velvety. Tube texture: Sparsely pubescent. Color: Petals, when opening and fully opened, upper surface: Close to 92D; random sectors and venation, N87A. Petals, when opening and fully opened, lower surface: Close to 92D; random sectors, N87A; venation, 79B. Throat: 145C; venation, 79A. Tube: 145C; random sectors, N87A; venation, 80A.

*Calyx.*—Arrangement: One star-shaped calyx tube with five sepals fused at the base per flower. Sepal length: About 1.4 cm. Sepal width: About 3.2 mm. Sepal shape: Elliptic. Sepal apex: Obtuse. Sepal margin: Entire. Sepal texture, upper and lower surfaces: Pubescent. Color, upper and lower surfaces: 144A.

*Peduncles.*—Length: About 2 cm. Diameter: About 1.3 mm. Angle: Upright and outwardly. Strength: Strong. Texture: Pubescent. Color: 144A tinted with N77A.

*Reproductive organs.*—Stamens: Quantity/arrangement: Five per flower. Stamen length: About 2.5 cm. Anther shape: Ellipsoidal. Anther size: About 2 mm to 1.5 mm. Anther color: 10D. Pollen amount: Moderate. Pollen color: 8D. Pistils: Quantity: One per flower. Pistil length: About 3 cm. Style color: 144D. Stigma shape: Transversely ellipsoidal. Stigma color: 144A. Ovary color: 144A. Seed/fruit: Seed and fruit development have not been observed on plants of the new *Petunia*.

Temperature tolerance: Plants of the new *Petunia* have been observed to tolerate temperatures from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Kumiyama 4' as illustrated and described.

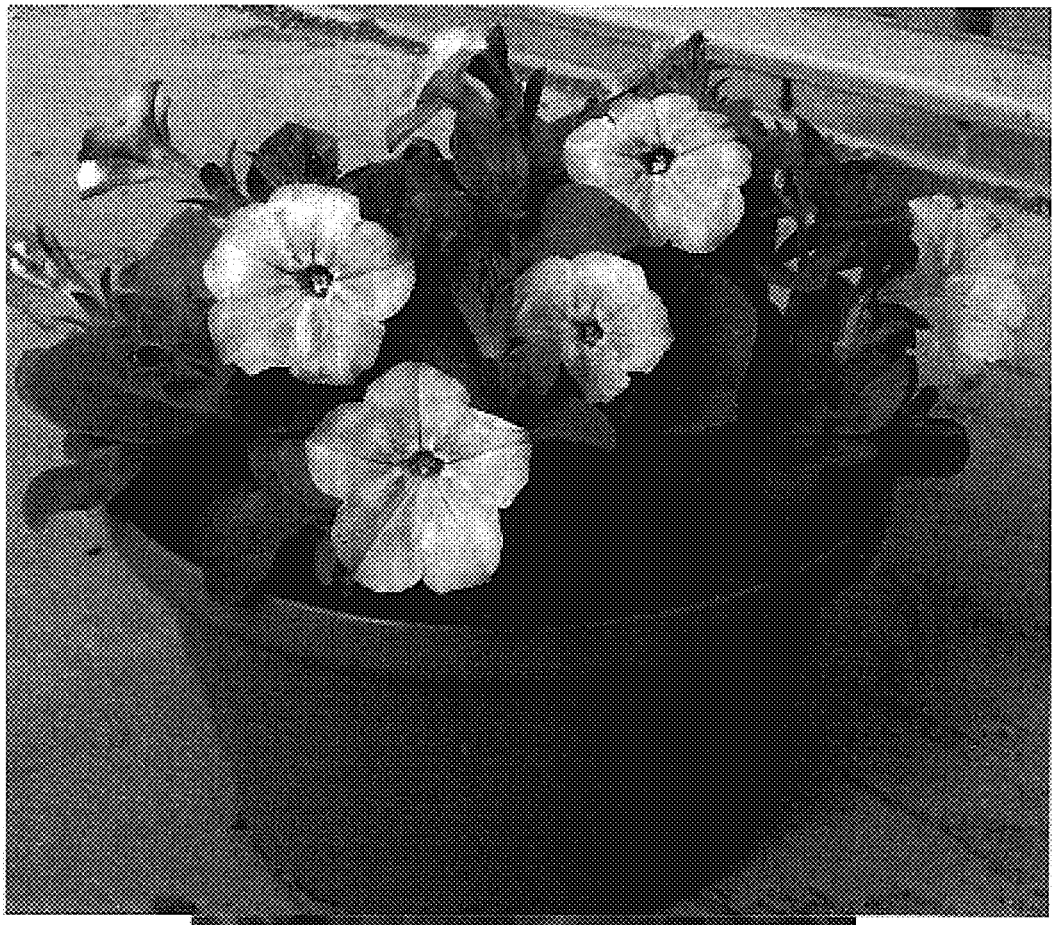
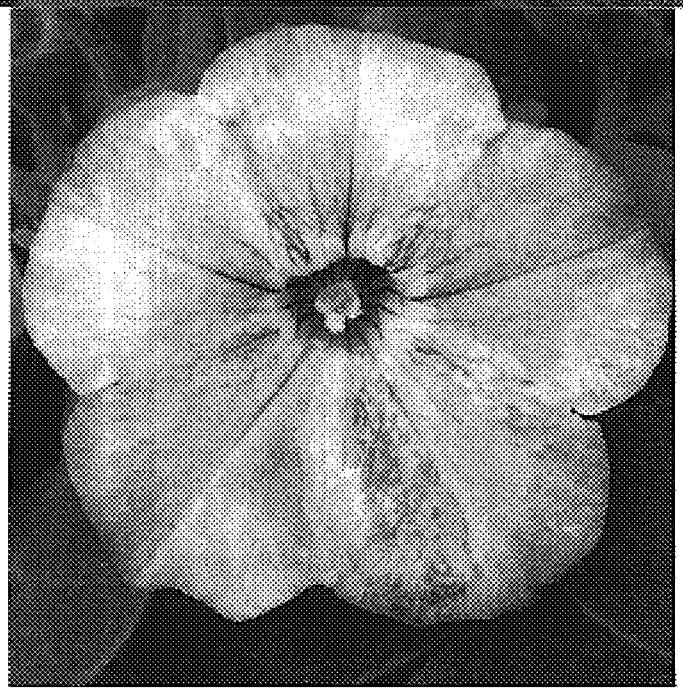

* * * * *